United States Patent [19]

Kleylein

[11] Patent Number: 4,700,698

[45] Date of Patent: Oct. 20, 1987

[54] KNEE ORTHOSIS

[76] Inventor: Horst Kleylein, Sudetenstrasse 13, D-8502 Zirndorf, Fed. Rep. of Germany

[21] Appl. No.: 811,835

[22] PCT Filed: Apr. 2, 1985

[86] PCT No.: PCT/DE85/00099

§ 371 Date: Dec. 5, 1985

§ 102(e) Date: Dec. 5, 1985

[87] PCT Pub. No.: WO85/04569

PCT Pub. Date: Oct. 24, 1985

[30] Foreign Application Priority Data

Apr. 5, 1984 [DE] Fed. Rep. of Germany ....... 3412772

[51] Int. Cl.⁴ ................................................ A61F 3/00
[52] U.S. Cl. .................................................. 128/80 C
[58] Field of Search ................. 128/80 C, 87 R, 80 R, 128/165, DIG. 20, DIG. 21; 2/24, 22, 16, 18; 264/222

[56] References Cited

U.S. PATENT DOCUMENTS 3,322,873  5/1967  Hitchcock ............................ 2/24 X
3,458,867  8/1969  Moore et al. .................... 128/165 X
3,742,517  7/1973  Bednarczuk et al. ......... 128/80 C X
4,217,893  8/1980  Payton ............................... 128/89 R
4,250,578  2/1981  Barlow .......................... 128/80 C X
4,425,912  1/1984  Harper .............................. 128/80 C
4,492,225  1/1985  Picolet et al. ..................... 128/89 R

FOREIGN PATENT DOCUMENTS 115029  8/1984  European Pat. Off. .
0027172  4/1981  Fed. Rep. of Germany .... 128/80 C

OTHER PUBLICATIONS

Hess, "Monatskurse für die ärztliche Fortbildung", vol. 33, 1983, issue 5, pp. 10–16.

Primary Examiner—Gregory E. McNeill
Attorney, Agent, or Firm—Spencer & Frank

[57] ABSTRACT

A knee orthosis includes a tubular stretchable fabric adapted to circumferentially surround the area of a wearer's knee, an annular pad secured to the fabric and adapted to surround the wearer's patella. Two lateral extensions constitute uninterrupted continuations of the annular pad and extend in opposite directions therefrom. The lateral extensions are located and dimensioned in length such that they terminate at areas beside the knee joint to leave uncovered a substantial zone of the posterior of the knee area.

10 Claims, 5 Drawing Figures

KNEE ORTHOSIS

BACKGROUND OF THE INVENTION

The invention concerns a knee orthosis consisting of a stocking-like stretchable knitted fabric with an annular pad, made of elastic incompressible material, situated in the area of the kneecap.

Such knee orthoses are known already, for example from the European patent specification No. 27 172 as well as from the periodical "Monatskurse für die ärztliche Fortbildung" (monthly courses of medical advanced training), volume 33, 1983, issue 5, pages 10–16. They serve the purpose of supporting or compressing the musculature of the knee joint and the tendinous bands in that area, as well as supporting the kneecap and fixing it in its position. The essential feature for the efficacy of the orthosis is the pad, which is incorporated into the fabric and which, according to the proposal of the above mentioned European patent specification, shall consist of an elastic, but incompressible silicone rubber or a material with the same elasticity and compression properties.

Similar knee orthoses are also described in the European patent application No. 115 029. This orthosis is not, however, a stocking-shaped orthosis, but a narrow bandage provided with holding ribbons, whose pad has the shape of a C or a circular ring. The holding ribbons for this pad are relatively small and, when used, they embrace the leg to be treated in the area of the knee joint.

In the present description the word "orthosis" shall mean an auxiliary apparatus which, generally stated, assists muscular activity and position. The word "pad" shall mean an additional support exerting pressure on certain joint or muscle regions.

The orthoses known before have fundamentally proved good. Nevertheless, in some cases disadvantages were found, consisting, for example, in a slipping of the orthosis during use, so that it could no longer fulfill its function. This disadvantage cannot be remedied simply by making the stocking-shaped fabric tighter, thus increasing the pressure, as especially upon bending of the joint more or less marked wrinkles will form, which will cause local pressures and constrictions. Furthermore, the already known orthoses with one-piece pads are not able to support the musculature of the knee joint laterally nor to center the kneecap.

SUMMARY OF THE INVENTION

It is an object of the invention to provide a knee orthosis with improved fit and supporting effect for a longer period of time, guaranteeing a wide pressure compensation or compression without any marked local reduced blood supply.

This object and others to become apparent as the specification progresses, are accomplished by the invention, according to which, briefly stated, the pad is provided with lateral extensions reaching up to the areas beside the knee joint. It is advantageous to extend these extensions so far that they cover the axis of the knee joint. On the one hand, the arrangement of such extensions increases the contact surface between pad and body, so that due to this measure the pad itself and thus the entire orthosis is more slip-proof. On the other hand, the lateral extensions do not only fix the kneecap, but they also support the muscle and band regions beside the kneecap, significantly improving patient care.

The orthosis has proved particularly advantageous for the therapy of contrapatiepatella. The blood supply of the peri-articular tissue is significantly improved. The feared atrophy when using the orthosis is avoided, as reflex inactivity patterns of the musculature around the knee joint cannot arise. As far as there are edemae or effusions in the joint, they will be resorbed more quickly, as a consequence of the unimpeded muscular movement.

It will be recognized that the orthosis stabilizes the knee joint over its layer of soft tissues, without hindering the natural movements of the joint. Local irritations such as pressure and reduced blood supply are avoided thanks to the wide pressure compensation.

The orthosis can also be applied in the therapy of stases in the knee joint or states of irritation following lesions, operations as well as chronically inflammatory alterations. The orthesis is of special advantage in the therapy of chondropathia patellae which is found mainly among young people, in particular among athletes.

A frequent cause of chondropathia patellae is the weakness of the medial quadriceps, i.e. a weakness of the inner branch of the great front muscle of the femur, which causes a dysbalance of the kneecap guidance. Through the muscle fibers of the medial branch of the quadriceps this dysbalance develops relatively fast after sparing the muscle of the femur or the knee, thus leading to a long-lasting disorder of the knee joint.

In order to reinforce the effect of the orthosis, according to a feature of the invention additional reinforcements are incorporated into the lateral extensions. These reinforcements may be made of elastic, but firm material, and may be cast or vulcanized into the pad. In tests good results were achieved with reinforcing laminae of softened polyvinyl chloride, fastened in the pad as indicated. In order to obtain a safe and intimate junction of the reinforcements with the pad material, according to a further feature of the invention the reinforcements are in the shape of flat disks provided with anchoring holes through which filaments of the pad material are passed.

According to still another advantageous feature of the invention, the side of the pad which when used faces the body, carries a bulgy raised part made of soft, compression-proof material in the area of the pad ring and in the vicinity of one of the extensions. This bulgy raised part increases the pressure in the respective place and serves, for example, the purpose of centering the kneecap more effectively. Furthermore, by means of an orthosis reinforced in this way the kneecap may be displaced towards the outer side, which may be useful, for example, in case of lesions of the kneecap back, in which case the retropatellar cartilage, during postoperative early mobilization can be only partially stressed.

The knee orthosis conventionally has a stocking-like stretchable knitted fabric (fabric tube) made of rubber and/or synthetic threads. The incorporated pad is made preferably of elastic, but incompressible silicone rubber. The pad has a thickness of approximately 5–7 mm, the ring width is approximately 25–30 mm. The hole in the middle of the annular pad is preferably oval, having a width of about 50 mm and a height of about 70 mm. The height of the lateral extensions is the same as the height of the ring hole, their lateral protrusion is, for example, 30 mm. It has to be emphasized that the protrusion may also be larger, according to the individual requirements.

An enlargement of the lateral protrusion of the extensions indicated in particular if the pad with its extensions shall reach beyond the axis of the knee joint. In this case the protrusion (width) on either side may amount to up to 70 mm.

The proposed pad is manufactured preferably of silicone rubber in a casting process. Casting is effected, for example, in a plaster mold made to measure according to the patient's individual requirements.

When manufacturing the pad in this way it is easy to incorporate the additional reinforcement laminae. In order to obtain an intimate junction between the laminae and the pad material, the laminae are perforated in various placed and then put in the liquid material which is already in the casting mold. The material will pass through the holes so that during the curing process thread-like bridges penetrating the reinforcement lamina will build up.

DESCRIPTION OF THE PREFERRED EMBODIMENT

Figure 1:
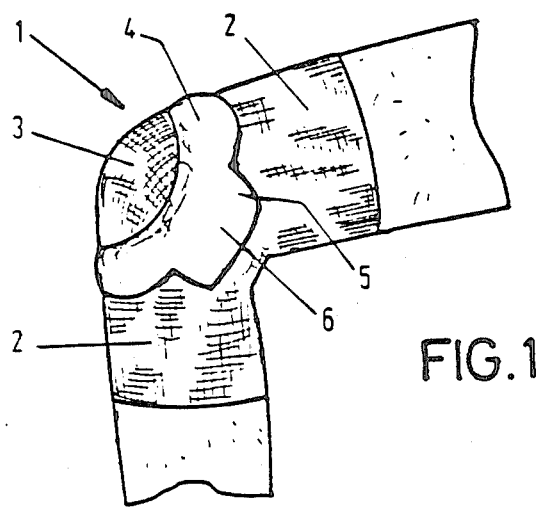
FIG. 1 is a schematic side elevational view of a preferred embodiment, depicted in use.
Figure 2:
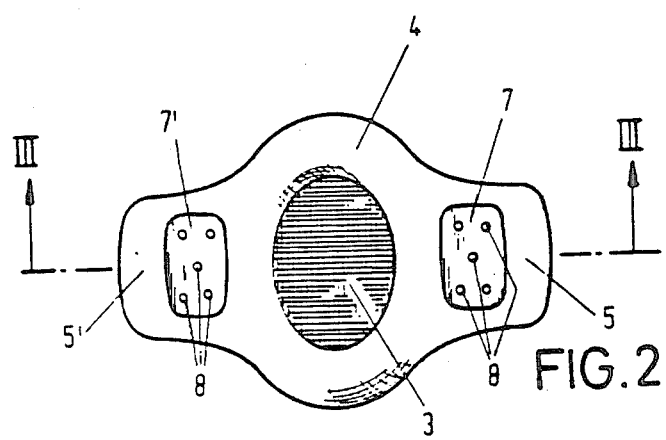
FIG. 2 is a top plan view of a component of the preferred embodiment.

The orthosis shown in FIGS. 1 and 2 is, as a whole, designated at 1. It conventionally comprises a stocking-like stretchable knitted fabric (fabric tube) 2 in which an annular pad 4, made of elastic, incompressible material, is situated in the area of the kneecap 3. The pad is provided with lateral extensions 5, 5' reaching to the areas on the side of the knee joint. The lateral extensions 5, 5' constitute uninterrupted continuations of the annular pad 4. FIG. 1 shows that these lateral extensions reach even beyond the axis 6 of the knee joint. As seen in FIG. 1, however, the lateral extensions 5, 5' leave uncovered a substantial zone of the posterior of the knee area.

Figure 3:
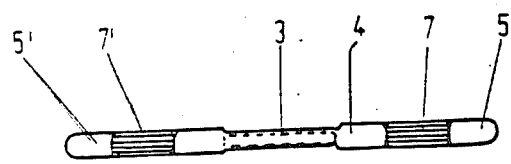
FIG. 3 is a sectional view taken along line III—III of FIG. 2.
Figure 4:
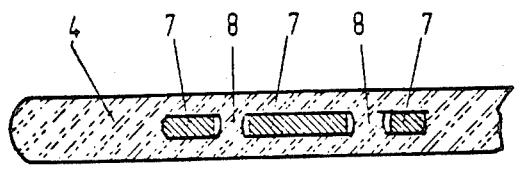
FIG. 4 is an enlarged detail of FIG. 3.

To increase the lateral pressure exerted by the pad, reinforcements 7 and 7' are incorporated in the lateral extension, as shown in FIGS. 2 and 3. The reinforcements are preferably made of an elastic, but firm material; they are cast or vulcanized into the pad. In other types of design it is also possible to produce the reinforcements by including pieces of tissue or the like or by incorporating compressed zones. It has proved advantageous, however, to make the reinforcements 7 in the shape of flat parts, provided with anchoring holes 8 through which filaments of the pad material are passed, as illustrated in FIG. 4 which shows a single reinforcement 7 with two anchoring holes 8. As seen, the material of the pad 4 has penetrated the holes 8 and constitutes thread-like fixing bodies to effect anchoring.

Figure 5:
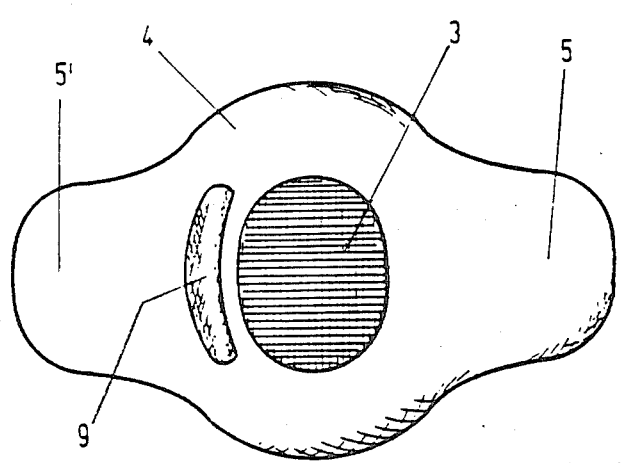
FIG. 5 is a bottom plan view of the preferred embodiment.

FIG. 5 shows the side of the pad which in use faces the patient's body. It can be seen that a bulgy raised part 9 is situated in the area of the pad 4 and close to the root of one of the extensions 5, 5'. This raised part 9 consists of a soft, pressure-resistant material, for example, softened polyvinyl chloride, or of silicon rubber. The bulgy raised part 9 is produced when casting the pad; it may, however, also be glued on or fixed otherwise.

It will be understood that the above description of the present invention is susceptible to various modifications, changes and adaptations, and the same are intended to be comprehended within the meaning and range of equivalents of the appended claims.

LEGEND 1 orthosis
2 knitted fabric
3 kneecap
4 pad
5, 5' lateral extensions
6 axis of the joint
7, 7' reinforcements
8 anchoring holes
9 bulgy raised part
(5 figures)

I claim:

1. In a knee orthosis including a tubular stretchable fabric adapted to circumferentially surround the area of a wearer's knee, an annular pad secured to said fabric and adapted to surround the wearer's patella, the improvement comprising two lateral extensions constituting uninterrupted continuations of said annular pad and extending in opposite directions therefrom; said lateral extensions being located and dimensioned in length such that they terminate at areas beside the knee joint to leave uncovered a substantial zone of the posterior of the knee area.

2. A knee orthosis as defined in claim 1, wherein said lateral extensions reach beyond the axis of the knee joint.

3. A knee orthosis as defined in claim 1, wherein said pad and said lateral extensions constitute a one-piece component consisting of an elastic, incompressible material.

4. A knee orthosis as defined in claim 3, wherein said elastic, incompressible material is a silicone rubber.

5. A knee orthosis as defined in claim 1, further comprising a reinforcing part carried by each said lateral extension.

6. A knee orthosis as defined in claim 5, wherein the reinforcing parts are of a firm, elastic material.

7. A knee orthosis as defined in claim 5, wherein said reinforcing parts are embedded in a respective said lateral extension.

8. A knee orthosis as defined in claim 7, wherein each said reinforcing part is flat and has throughgoing holes through which material of the respective said lateral extension passes.

9. A knee orthosis as defined in claim 1, wherein said annular pad has a face arranged to be oriented towards the wearer's body; further comprising a raised portion forming part of said annular pad and projecting from said face; said raised part adjoining one of said lateral extensions, and being of a soft, compression-resistant material.

10. A knee orthosis as defined in claim 9, wherein said raised portion is of elongated, curved shape and extends partially about a central opening of the annular pad.

* * * * *